US011446605B2

(12) United States Patent
Besarati et al.

(10) Patent No.: US 11,446,605 B2
(45) Date of Patent: Sep. 20, 2022

(54) APPROACH TO COST EFFECTIVE CARBON CAPTURE FROM AIR BY PRODUCING CARBON NEGATIVE WATER

(71) Applicant: CARBON CAPTURE, Pasadena, CA (US)

(72) Inventors: Saeb M. Besarati, Pasadena, CA (US); Michael A. Giardello, Pasadena, CA (US); William Gross, Pasadena, CA (US); Andrea Pedretti, Pasadena, CA (US)

(73) Assignee: CARBON CAPTURE, Pasadena, CA (US)

( * ) Notice: Subject to any disclaimer, the term of this patent is extended or adjusted under 35 U.S.C. 154(b) by 89 days.

(21) Appl. No.: 17/099,146

(22) Filed: Nov. 16, 2020

(65) Prior Publication Data

US 2021/0146299 A1 May 20, 2021

Related U.S. Application Data

(60) Provisional application No. 62/935,868, filed on Nov. 15, 2019.

(51) Int. Cl.
*B01D 53/62* (2006.01)
*B01D 53/26* (2006.01)
(Continued)

(52) U.S. Cl.
CPC ............ *B01D 53/261* (2013.01); *B01D 53/62* (2013.01); *C01B 3/045* (2013.01);
(Continued)

(58) Field of Classification Search
CPC .. B01D 2257/504; B01D 53/62; B01D 53/18; B01D 53/73; B01D 53/77; B01D 53/80;
(Continued)

(56) References Cited

U.S. PATENT DOCUMENTS 7,422,993 B2 9/2008 Takewaki et al.
9,550,142 B2 1/2017 Roestenberg et al.
(Continued)

FOREIGN PATENT DOCUMENTS

EP    1417995 A1    5/2004
WO   2017/140954 A1   8/2017
WO   2019152962 A2   8/2019

OTHER PUBLICATIONS

Jain et al., "The World Around Bottled Water," Bottled and Packaged Water, vol. 4: The Science of Beverages, 2019, pp. 39-61 (Elsevier).

(Continued)

*Primary Examiner* — Sharon Pregler
(74) *Attorney, Agent, or Firm* — J.A. Lindeman & Co. PLLC

(57) ABSTRACT

The invention relates to integrated methods for direct capture of carbon dioxide and water from the atmosphere and their conversion into value-added products in an economical and carbon negative fashion. In one embodiment of the present invention, a portion of the water captured in a DAC process is treated, bottled, and sold as value-added drinking water, thereby offsetting the cost of the capture process. Preferably the drinking water is bottled in low carbon footprint packaging to offer cost benefit while maintaining overall carbon neutrality or negativity. In other embodiments of the invention, a portion of the captured water is split by photovoltaic electrolysis into hydrogen and oxygen as further value-added products. In other embodiments of the present invention, a portion of the captured carbon dioxide is chemically reduced, preferably utilizing hydrogen from the aforementioned photovoltaic-electrolysis process, to produce methanol for use as a carbon-advantaged fuel.

11 Claims, 5 Drawing Sheets

(51) Int. Cl.
  *C01B 3/04* (2006.01)
  *C25B 1/04* (2021.01)
  *C07C 31/04* (2006.01)
  *C07C 29/151* (2006.01)
  *C01B 13/02* (2006.01)

(52) U.S. Cl.
  CPC ...... *C01B 13/0207* (2013.01); *C07C 29/1518* (2013.01); *C07C 31/04* (2013.01); *C25B 1/04* (2013.01); *B01D 2257/504* (2013.01)

(58) Field of Classification Search
  CPC ...... B01D 5/009; Y02P 20/151; Y02P 20/133; Y02P 20/152; Y02P 30/00; Y02P 60/20
  See application file for complete search history.

(56) References Cited

U.S. PATENT DOCUMENTS

| | | |
|---|---|---|
| 2011/0203311 A1 | 8/2011 | Wright et al. |
| 2017/0113184 A1* | 4/2017 | Eisenberger ............ B01J 20/262 |
| 2019/0127253 A1 | 5/2019 | Thomas et al. |
| 2021/0120750 A1* | 4/2021 | Bourhis ............ B01D 53/1475 |

OTHER PUBLICATIONS

Burtch et al., "Water Stability and Adsorption in Metal-Organic Frameworks," Chemical Reviews, 2014, 114, 10575-10612.
Knox et al., "Investigation of Desiccants and CO2 Sorbents for Exploration Systems 2016-2017," 47th International Conference on Environmental Systems, Jul. 16-20, 2017, Charleston, South Carolina, USA (ICES-2017-188).
Chen et al., "Progress toward Commercial Application of Electrochemical Carbon Dioxide Reduction," Chem, 2018, 4, 2571-2586.
Sanz-Pérez et al., "Direct Capture of CO2 from Ambient Air," Chemical Reviews, 2016, 116, 11840-11876.
Goeppert et al., "Air as the renewable carbon source of the future: an overview of CO2 capture from the atmosphere," Energy & Environmental Science, 2012, 5, 7833-7853.
Fasihi et al., "Techno-economic assessment of CO2 direct air capture plants," Journal of Cleaner Production, 2019, 224, 957-980.
Zhou et al., "Atmospheric Water Harvesting: A Review of Material and Structural Designs," ACS Materials Letters, 2020, 2, 671-684.
Bagheri, "Performance investigation of atmosphere water harvesting systems," Water Resources and Industry, 2018, 20, 23-28.
International Search Report and Written Opinion in International Application No. PCT/US2020/060728, dated Feb. 11, 2021.

* cited by examiner

APPROACH TO COST EFFECTIVE CARBON CAPTURE FROM AIR BY PRODUCING CARBON NEGATIVE WATER

RELATED APPLICATIONS

This application claims the benefit of U.S. Provisional Patent Application No. 62/935,868, filed Nov. 15, 2019, the contents of which are incorporated herein by reference.

TECHNICAL FIELD

The invention relates to integrated methods for direct capture of carbon dioxide and water from the atmosphere and their conversion into value-added products in an economical and carbon negative fashion.

BACKGROUND

Global warming is posing devastating effects on our climate, health, and communities. Coastal flooding due to rising sea levels, extended wildfire seasons, as well as more destructive hurricanes are the direct impacts of climate change. Moreover, global food and water security are at stake. There is a consensus among scientists that global warming is directly linked to the increase in the level of greenhouse gases in the atmosphere.

Carbon dioxide ($CO_2$) is a major greenhouse gas, which its concentration in the atmosphere has sharply increased over the past century due to burning fossil fuels. On the other hand, shifting our energy supply to completely renewable-based is not possible in the near term and requires technological advancements and global investments. Therefore, there is a growing need for technologies that can capture carbon dioxide from the flue gas of the power plants or other industrial processes as well as from ambient air. The latter is known as direct air capture (DAC). E. S. Sanz-Pérez, C. R. Murdock, S. A. Didas, and C. W. Jones in *Chemical Reviews*, 2016, 116, 11840-11876 and A. Goeppert, M. Czaun, G. K. Surya Prakash, and G. A. Olah in *Energy & Environmental Science*, 2012, 5, 7833-7853 review recent status and issues around DAC.

The process of DAC is energy-intensive, which is due to the low concentration of $CO_2$ in the air. This leads to high capital and operational costs. M. Fasihi, O. Efimova, and C. Breyer in *Journal of Cleaner Production*, 2019, 224, 957-980 discuss projected economics of large-scale DAC plants and estimate an approximate current (2020) cost of $300 per ton of $CO_2$ removed.

Moreover, the system needs to be oversized in carbon capture capacity to offset the $CO_2$ released during the process if the input energy is supplied by burning fossil fuels. On the other hand, the present incentives for capturing $CO_2$ set by various governmental entities are not high enough to pay for the cost of the system. For example, 26 U.S. Code § 45Q provides for a tax credit of up to only $35 to $50 per ton $CO_2$ captured in 2026 (and even less in the years before that). Further income may be realized from the sale of carbon credits but that it is still not currently sufficient to achieve even the break-even point (the monthly average price for California ARB LCFS credits were only $192 per ton $CO_2$ for calendar year 2019—see https://ww3.arb.ca.gov/fuels/lcfs/credit/lrtmonthlycreditreports.htm). Therefore, finding an appropriate source of income to make developments of DAC possible is a challenge facing this industry.

On the contrary to carbon dioxide, water is a scarce and valuable element. Humans need water to survive and thrive. Drinking water resources are becoming short due to growing demand and global warming. Therefore, humans are becoming more dependent on alternate water sources such as water desalination technologies. However, the water desalination process is very energy-intensive, which results in releasing carbon dioxide into the atmosphere. Moreover, the water desalination plants need to be located next to a water source such as the ocean, which is not possible for many regions of the world. In addition, there are serious concerns about discharging the brine to the environment. Recently, there has been a growing interest in capturing water directly from the air—see, for example, Zhou, et al. in *ACS Materials Letters*, 2020, 2, 671-684 and Bagheri in *Water Resources and Industry*, 2018, 20, 23-28. The main advantage is that it can potentially be located anywhere on earth. The current state-of-the-art is based on cooling condensation and desiccation. Both of these processes require significant amounts of energy and are not cost-effective at large scale.

SUMMARY OF THE INVENTION

In this patent, an alternative integrated approach is presented, which is based on the combination of capturing water and carbon dioxide in such a way to make the whole process both carbon negative and cost-effective. In other words, this approach will address two life threatening challenges, i.e. global warming and water scarcity, in a manner that is achievable and scalable in the near future. In one embodiment of the present invention, a portion of the water captured in a DAC process is treated, bottled, and sold as value-added drinking water, thereby offsetting the cost of the capture process. In another embodiment of the present invention, the drinking water is bottled in low carbon footprint packaging to offer cost benefit while maintaining overall carbon neutrality or negativity. In another embodiment of the present invention, the relative amounts of the drinking and non-drinking water are balanced to provide optimal profitability while maintaining overall carbon negativity. In other embodiments of the present invention, a portion of the captured water is split by photovoltaic electrolysis into hydrogen and oxygen as further value-added products. In other embodiments of the present invention, a portion of the captured carbon dioxide is chemically reduced, preferably utilizing hydrogen from the aforementioned photovoltaic-electrolysis process, to produce methanol as a further value-added product or for use as a carbon-advantaged fuel for use in transporting the drinking water and/or other value-added products of the present invention to their applicable end-markets.

BRIEF DESCRIPTION OF THE DRAWINGS

These and other objects, features and attendant advantages of the present invention will be more fully appreciated or become better understood when considered in conjunction with the accompanying drawings, wherein.

DETAILED DESCRIPTION OF THE INVENTION

Figure 1:
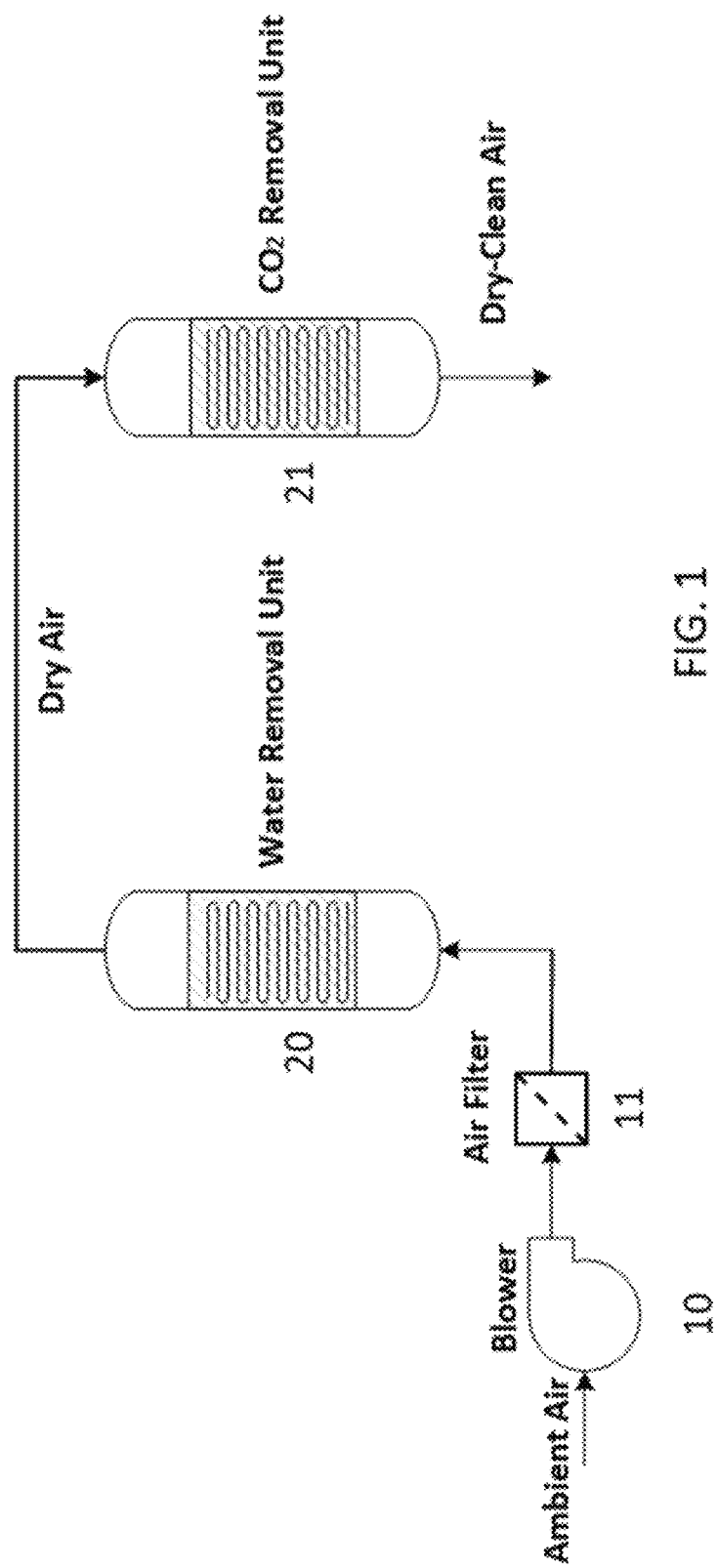
FIG. 1 is a schematic illustration of a basic two-stage DAC process to capture water and $CO_2$ from ambient air to produce dry-clean air.

The process of capturing $CO_2$ on solid sorbents is well-known. At room temperature and under dry condition, zeolites perform exceptionally well. However, the adsorption capacity deteriorates with an increase in temperature and in the presence of moisture. In other words, the available sites on zeolite are mostly occupied by water molecules when there is moisture in the air, leading to poor performance in $CO_2$ capture. Furthermore, a large amount of energy is required to regenerate the sorbent by releasing the water captured in the process. Therefore, air must be dried first before entering the $CO_2$ capture unit to about or less than 0.3% relative humidity (RH) and preferably less than 0.2% RH. FIG. 1 illustrates the basic operation of such a two-stage DAC process. Ambient air pressurized by a blower 10 passes through a filter 11 to remove particulates. The filtered air is then conducted to a water removal unit 20 to remove water to reduce the moisture content of the air before it enters the $CO_2$ removal reactor. The water removal unit can be a desiccant bed of silica gel, aluminum phosphate, etc. Alternatively, it can operate based on principles of cooling condensation. The dry air is then conducted to a $CO_2$ removal unit 21 where carbon dioxide is removed from the stream. The $CO_2$ removal unit contains a solid bed of a $CO_2$ sorbent. The water and $CO_2$ removal units may each independently be packed bed, fluidized bed, or monolithic reactors. The dry-clean air is then released back to the atmosphere.

Desiccants that may be used for water capture include silica gels, alumino-silica gels, various zeolites or molecular sieves (e.g., 3 Å molecular sieves like Grace MS 564 or 4 Å molecular sieves like Grace MS 514 or UOP UI-94), activated alumina, metal-organic framework (MOF) materials (nonlimiting examples of which those described by Burtch, et al. in *Chemical Reviews*, 2014, 114, 10575-10612 and by Yaghi, et al. in International Publication No. WO 2019/152962 A2), metal aluminophosphates (such those described by Takewaki, et al. in U.S. Pat. No. 7,422,993B2) or the AQSOA advanced zeolite products from Mitsubishi Chemical Corporation. Suitable $CO_2$ sorbents include various zeolites or molecular sieves, nonlimiting examples of which include 5 Å molecular sieves like Grace MS 522 or BASF 5A and 10 Å molecular sieves like BASF 13X. The properties and performance of several useful desiccants and $CO_2$ sorbents are described in J. C. Knox, D. W. Watson, and T. J. Giesy, 47$^{th}$ International Conference on Environmental Systems, 16-20 Jul. 2017, Charleston, S.C., USA (ICES-2017-188).

Figure 2:
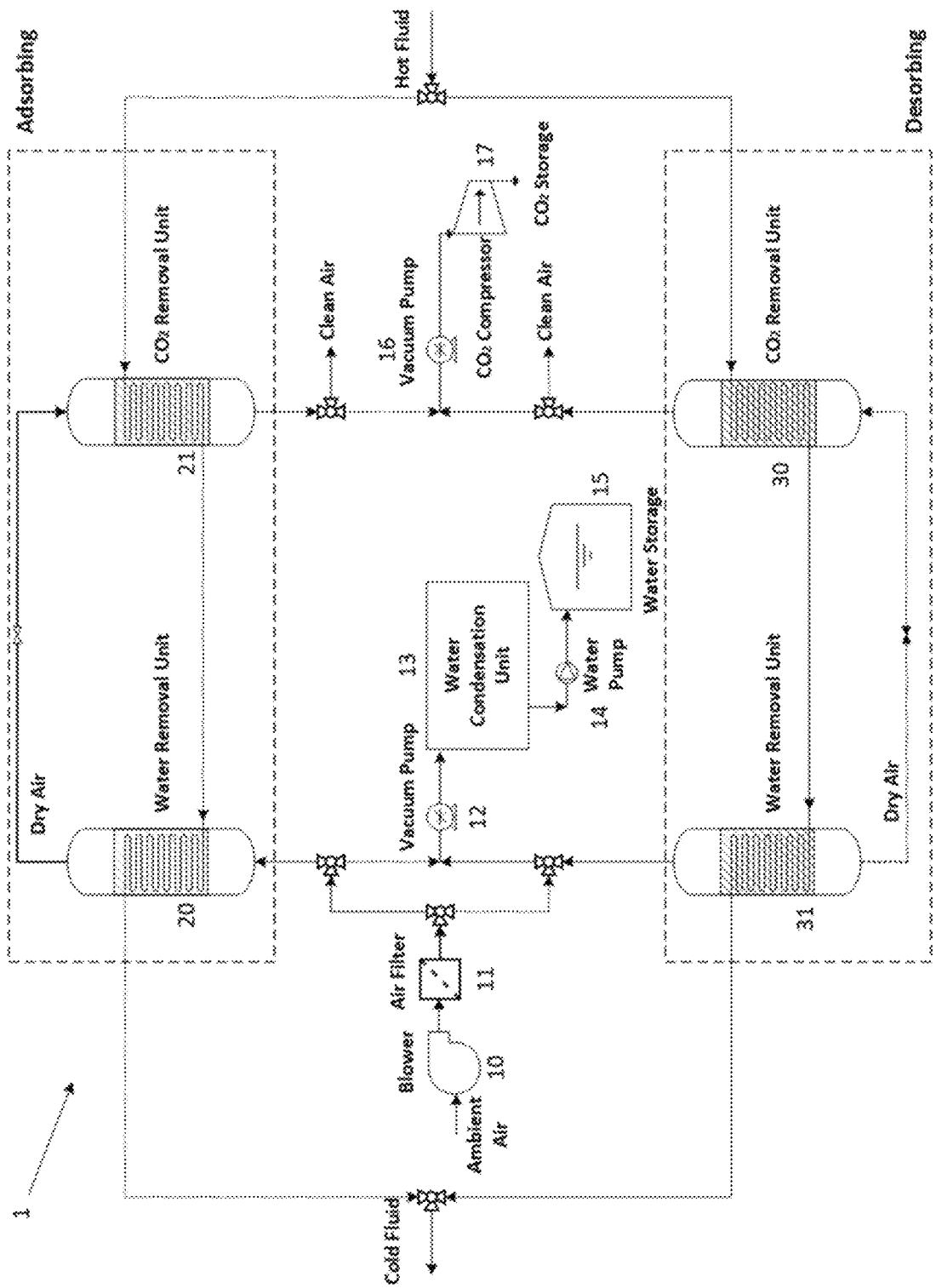
FIG. 2 is a schematic illustration of a continuous adsorption-desorption DAC process with parallel reactors operating alternatingly in adsorption and desorption modes.

Since the sorbents used in the water and $CO_2$ removal units need to be frequently regenerated to release the captured water and $CO_2$, two or more parallel units are generally operated in sequence for continuous DAC operation. While a combination of water and $CO_2$ capture units are operating in the adsorbing phase, at least one more set of reactors are desorbing the captured water and $CO_2$ to make the continuous operation of the plant possible. Once the adsorption phase is complete, water and $CO_2$ are removed from the reactors by providing heat. Moreover, applying a vacuum to the reactors can enhance the desorption process. FIG. 2 shows the details of such a DAC carbon capture unit, generally designated by reference number 1. This figure shows two parallel paths that go through alternating adsorption-desorption cycles. The components 20 and 21 are adsorbing water and $CO_2$ from the atmosphere respectively, while units 30 and 31 are releasing the adsorbed $CO_2$ and water in the previous stage for storage and further processing. The alternating paths are shown with the solid and dashed lines. Carbon dioxide is released from the $CO_2$ Removal Unit 30 by temperature swing, vacuum swing, or a combination of the two and is then pressurized using a $CO_2$ compressor 17 for storage or further use. Water removed from the Water Removal Unit 31 by temperature swing, vacuum swing, or a combination of the two and is sent to a condensation unit 13. The liquid water produced by this process is stored in the water storage tanks 15. The solid lines show the operating state while the dashed lines depict the next phase when the operating conditions are reversed.

Figure 3:
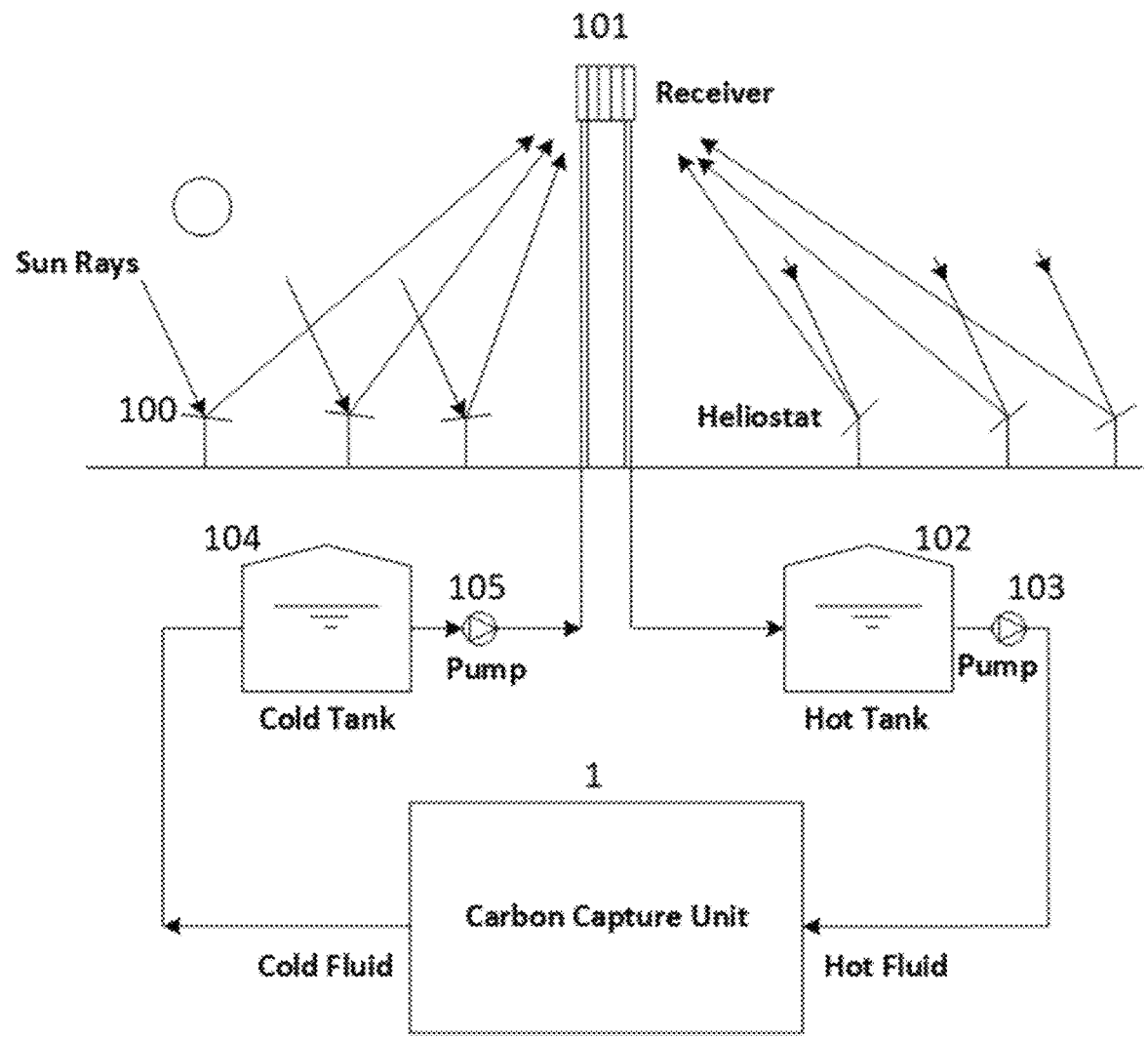
FIG. 3 presents the main components of a solar thermal power unit to provide heat for the carbon capture unit.

The process of water and $CO_2$ desorption requires heat. In some embodiments, the heat is supplied by concentrating solar energy rather than burning fossil fuels. The desorption temperature of the system is generally between 100° C. to 200° C. This temperature range can be achieved using low-cost heliostats and a receiver. In addition, pressurized water can be directly stored in two tanks providing continuous heat to the process. FIG. 3 presents the basic components of a solar thermal power unit providing heat to the Carbon Capture Unit 1. Sun rays are reflected by Heliostats 100 that tracks the sun throughout the day. The reflected beams are concentrated on a solar receiver 101 where the heat transfer fluid is heated. The heat transfer fluid can be water, oil, or molten salt. The high temperature fluid is stored in a Hot Tank 102 for 24/7 operation. The high temperature fluid is pumped 103 to the heat exchangers inside the Carbon Capture Unit 1 where heat is supplied to the reactors undergoing desorption. The cold fluid exiting the Carbon Capture Unit 1 is sent to a Cold Tank 104. The fluid from the Cold Tank 104 is pumped 105 back to the Solar Receiver 101 to be reheated.

Figure 4:
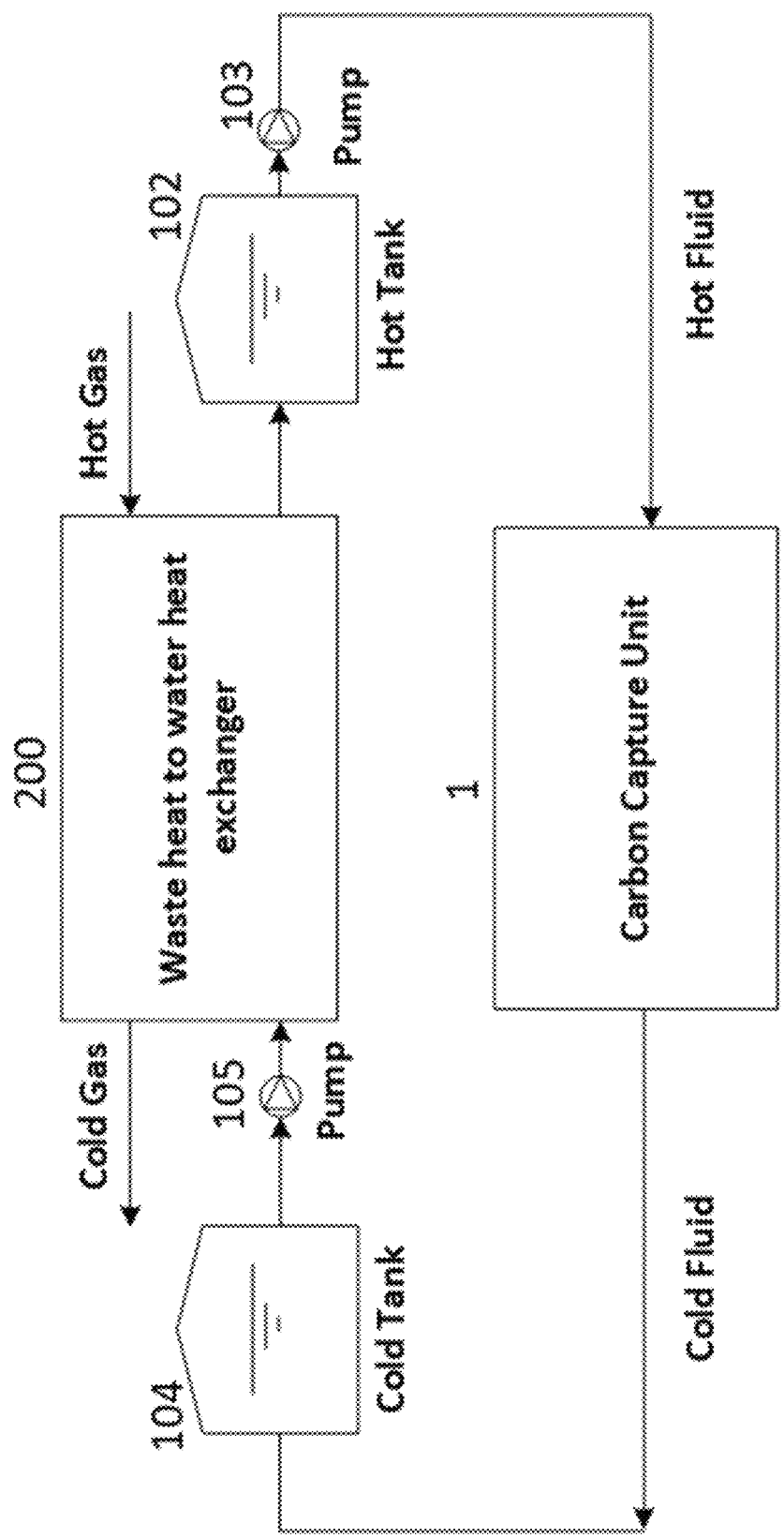
FIG. 4 illustrates the use of waste heat from external resources to operate the carbon capture unit.

Alternatively, certain DAC installations may be located near other plants or processes such that heat can be supplied by the waste heat from such other plants or processes. FIG. 4 illustrates the use of such waste heat to provide thermal energy for the Carbon Capture Unit 1. The hot gas exiting other plants or processes is directed to a heat exchanger 200 where its thermal energy is transferred to a heat transfer fluid. Depending on the availability of the heat source, the heat transfer fluid can be directly sent to the Carbon Capture Unit 1 or it can be stored in the storage tanks 102, 104.

Carbon-Water Capture Economy

The number of water molecules present in atmospheric air is much higher than the carbon dioxide molecules. At the ambient condition of 30° C. and 30% relative humidity, there is about 13 tons of water in the air for every ton of carbon dioxide. Therefore, applying the process described in the previous section on a large scale can potentially lead to a large water production facility. On the other hand, by taking the capital cost and energy requirement into consideration, it will not be cost-effective to sell water as a commodity. For example, water from desalination costs approximately $1,000-2,000 per acre foot (https://e360.yale.edu/features/as-water-scarcity-increases-desalination-plants-are-on-the-rise), a price considered high for commodity water. Therefore, even if all of the water produced could be sold at this pricing, it would equate to only about an additional $10-20 of revenue per ton of $CO_2$ recovered (assuming 13 tons of sellable water per ton of removed $CO_2$).

The water recovered from the DAC process will be of good purity and only slight modifications will be required to be made to achieve water suitable for use as drinking water (e.g., see Jain, et al. in *Bottled and Packaged Water, Volume 4: The Science of Beverages*, pages 39-61, Elsevier, 2019). In 2019, the average wholesale price for bottled water in the U.S. was approximately $1.35 per gallon (see Rodwin in *Bottled Water Reporter*, July/August 2020, pages 13-21, https://www.bottledwater.org/public/2019BWstats_BMCarticle_BWR_JulyAug2020.pdf) which would equate to gross revenues of over $4,000 per ton of $CO_2$ recovered. On the other hand, although it is highly profitable, bottling the whole produced water is not a feasible approach, as more carbon dioxide will be generated during the bottling and transportation than what is captured earlier by the system. The alternative approach is to find the optimal approach to make the whole process carbon-neutral to carbon-negative while profitable.

In this approach, the carbon footprint of the bottling process and transportation is calculated. Using sustainable (compostable or biodegradable) containers are favorable due to low carbon footprint. Moreover, using electric vehicles and biofuel trucks reduces the carbon footprint of transportation. If only an optimal fraction of total water produced in the process is sold to the market in bottled form that makes the whole process from production to delivery carbon negative. The rest of the water is sold at a low price to communities for non-drinking applications such as agriculture. The $CO_2$ captured from the air can be sequestered or sold in the market or utilized in other applications to make additional profit.

Figure 5:
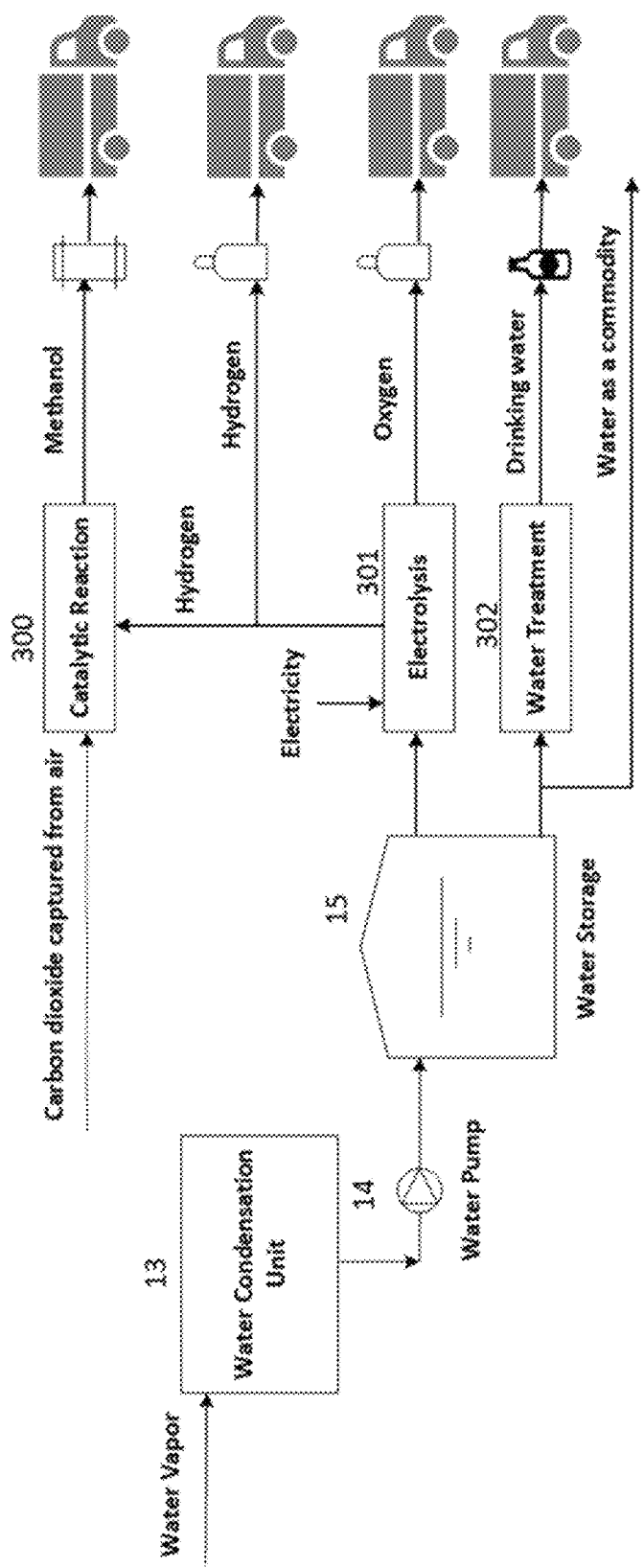
FIG. 5 presents different potential sources of revenue for the direct air capture plant.

One other interesting approach is to use $CO_2$ for producing methanol or other hydrocarbon fuels (see, for example, Chen, et al. in *Chem*, 2018, 4, 2571-2586). The excess water captured during the process is electrolyzed using electricity generated from photovoltaic (PV) power plant to produce hydrogen and oxygen. The generated hydrogen can be used to reduce the captured $CO_2$, which is a well-known chemical process. The final products are hydrogen, oxygen, and methanol that can be sold in the market. Methanol can be used as a feedstock for the chemical industry or used as a fuel in the transportation sector. FIG. 5 illustrates different products from the direct air capture plant that can be sold to provide additional revenues through further integration. A fraction of the water in the storage tanks 15 is sent to a Water Treatment Unit 302 where it is treated to meet the standards of drinking water. The drinking water is packaged and sold as carbon-negative water which provides an excellent source of revenue. The rest of water can be sold as a commodity and/or it can be sent to an Electrolysis unit 301 where hydrogen and oxygen are generated. The hydrogen and oxygen can be sold in the market. Alternatively, the hydrogen produced during the process and the $CO_2$ captured from the atmosphere can go through a Catalytic Reaction 300 to produce methanol. Methanol can be sold in the market, further processed to create other chemicals, or used as a fuel for the trucks delivering carbon-negative water.

The total revenue generated by the described approach is mainly dominated by selling the bottled waters. Not only it is a great source of revenue which allows the development and expansion of carbon capture facilities, but it will also provide an excellent opportunity for consumers to participate in the cause of cooling the planet. Consequently, it makes the employment of DAC possible at large scales. In addition, the air is the only source which is equally distributed anywhere on the earth. Therefore, the system can be utilized at any location addressing global warming and water scarcity problems simultaneously.

What is claimed is:

1. A method to produce water and dry-clean air comprising the steps of:
    (a) removing water from ambient air to produce a dry air stream;
    (b) removing $CO_2$ from the dry air stream to produce dry-clean air;
    (c) recovering the removed water;
    (d) treating a portion of the recovered water for use as drinking water; and
    (e) using or selling the remainder of the recovered water for non-drinking applications.

2. The method of claim 1 further comprising the steps of:
    (a) recovering the removed $CO_2$; and
    (b) sequestering, selling, or using the recovered $CO_2$ in other applications.

3. The method of claim 2 further comprising the step of electrolyzing a portion of the recovered water to produce hydrogen and oxygen.

4. The method of claim 3 further comprising the step of using a portion of the hydrogen produced to chemically reduce a portion of the recovered $CO_2$ to produce methanol.

5. The method of any of claims 2-4 wherein:
    (a) the water removal step is performed by passing the ambient air through a first solid sorbent material;
    (b) the $CO_2$ removal step is performed by passing the dry air stream through a second solid sorbent material;
    (c) the adsorbed water is desorbed from the first solid sorbent material by treatment with heat; and
    (d) the adsorbed $CO_2$ is desorbed from the second solid sorbent material by treatment with heat.

6. The method of claim 5 wherein concentrated solar power is utilized as the source of the heat used for desorbing the adsorbed water and adsorbed $CO_2$.

7. A system to produce carbon-advantaged drinking water and dry-clean air comprising:
    (a) a water removal unit capable of removing water from ambient air to produce a dry air stream;
    (b) a $CO_2$ removal unit capable of removing $CO_2$ from the dry air stream to produce dry-clean air;
    (c) a water condensation unit capable of recovering and storing the removed water;
    (d) a $CO_2$ recovery unit capable of recovering and storing the removed $CO_2$; and
    (e) a water treatment unit capable of purifying and bottling the recovered water for use as drinking water.

8. The system of claim 7 further comprising an electrolysis unit capable of converting a portion of the recovered water into hydrogen and oxygen.

9. The system of claim 8 wherein the electrolysis unit utilizes a photovoltaic-electrolysis process.

10. The system of claims 8 or 9 further comprising a catalytic reaction unit capable of converting recovered $CO_2$ and hydrogen into methanol.

11. The system of claim 7 wherein the amount of the recovered water purified for use as drinking water is selected to maintain carbon neutrality for the overall process.

* * * * *